United States Patent [19]

Lyons

[11] 4,182,722

[45] Jan. 8, 1980

[54] ION-EXCHANGED TRANSITION METAL CATALYSTS FOR THE DIRECT OXIDATION OF OLEFINS TO EPOXYALCOHOLS

[75] Inventor: James E. Lyons, Wallingford, Pa.

[73] Assignee: Sun Ventures, Inc., St. Davids, Pa.

[21] Appl. No.: 617,907

[22] Filed: Sep. 29, 1975

Related U.S. Application Data

[63] Continuation-in-part of Ser. No. 375,195, Jun. 29, 1973, abandoned.

[51] Int. Cl.$^2$ .......................................... C07D 301/06
[52] U.S. Cl. ................................................ 260/348.33
[58] Field of Search .................... 260/348.5 V, 348.33

[56] References Cited

U.S. PATENT DOCUMENTS

| | | | |
|---|---|---|---|
| 3,259,638 | 7/1966 | Allison | 260/348.5 V |
| 3,629,294 | 12/1971 | Sun | 260/348.5 V |
| 3,641,066 | 2/1972 | Rouchaud et al. | 260/348.5 V |

FOREIGN PATENT DOCUMENTS

| | | | |
|---|---|---|---|
| 1280234 | 10/1968 | Fed. Rep. of Germany | 260/348.5 V |
| 40953 | 9/1965 | German Democratic Rep. | 252/455 Z |
| 1150277 | 4/1969 | United Kingdom | 252/455 Z |

OTHER PUBLICATIONS

K. Allison et al., I & EC Product Research and Development, vol. 5, No. 2, Jun. 1966, pp. 166–173.
R. Hiatt, Oxidation—Techniques and Applications in Organic Synthesis, edited by Robert L. Augustine (1971), pp. 131, 133, 137–139.
E. S. Gould et al., Jour. of Catalysis, vol. 13 (1969), pp. 238–244.

*Primary Examiner*—Norma S. Milestone
*Attorney, Agent, or Firm*—J. Edward Hess; Donald R. Johnson; Donald R. Johnson

[57] ABSTRACT

Acylic or cyclic epoxyalcohols can be prepared by direct oxidation of an olefin when there is employed an ion-exchanged bimetallic catalyst, wherein one metal is from Groups IB or VIII, and the other from Group V.

14 Claims, No Drawings

ION-EXCHANGED TRANSITION METAL CATALYSTS FOR THE DIRECT OXIDATION OF OLEFINS TO EPOXYALCOHOLS

CROSS-REFERENCE TO RELATED CASES

This application is a continuation-in-part of Ser. No. 375,195, filed June 29, 1973 now abandoned.

BACKGROUND OF THE INVENTION

This invention relates to a novel method for the preparation of epoxyalcohols. More particularly, this invention is directed to the oxidation of acyclic or cyclic olefins to form the corresponding epoxyalcohols in the presence of an ion-exchanged bimetallic catalyst in which the metals are valence-bonded to an anionic support.

Use of the aforedescribed catalyst in the process of this invention is particularly advantageous in that no cocatalysts and/or hydroperoxide initiators need be employed, thereby providing an economical, soluble system which requires only relatively low concentrations of catalyst to be effective.

The epoxyalcohols of this invention can easily be converted into diols by hydrogenation (equation 1), and into triols (equation 2) by hydrolysis.

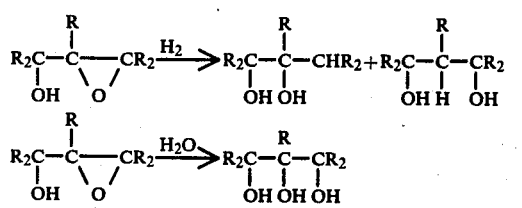

Both diols and triols are well known commercial products. These materials have found utility in the antifreeze market, in the preparation of alkyd resins, new synthetic fibers, synthetic polyester rubbers, solvents, humectants, lubricants and explosives (Mellan, "Polyhydric Alcohols", McGregor and Werner, Washington, D.C 1962).

The utility of the epoxy alcohol derived from cyclohexene has been disclosed in co-pending application, Ser. No. 457,045, filed April 1, 1974, namely, in the production of catechol and resorcinol. A specific utility for the epoxy alcohol derived from tetramethylethylene is the production of pinacol vial hydrogenation:

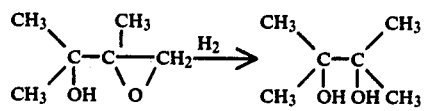

Pinacol is a useful monomer, being converted by heat and pressure into dimethylbutadiene which forms synthetic rubber when polymerized. (Mellan, "Polyhydric Alcohols"), (supra). 1,3-butane diol and 2,3-butanediol are commercial solvents having high volume utility and may be derived from 1-methyl-1-hydroxy-1,2-epoxy-propane:

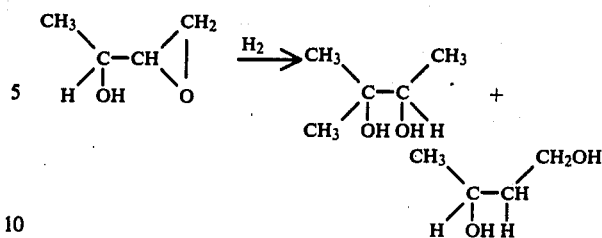

Hexylene glycol is another useful commercial solvent which would be formed by hydrogenation of 2-methyl-2-hydroxy-3,4-epoxypentane an epoxyalcohol derived from 1-methylpentene-2:

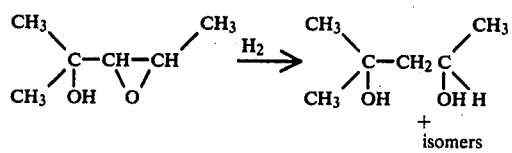

All the epoxyalcohols prepared in the examples can be converted to triols. Triols are generally usely as plasticizers and in the manufacturing of alkyd resins and in adhesives. Such diverse triols as 1,2,6-hexanetriol and tetramethylolpropene are effective in all three applications.

In addition, pyrogallol is a commercial product used as an inhibitor and in other applications pyrogallol can be prepared from the epoxyalcohol via the following equation:

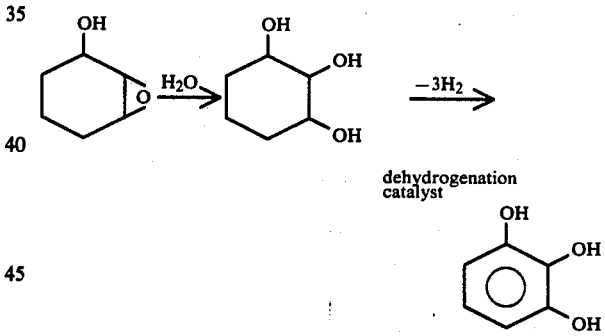

Cyclic olefins, such as cyclohexene, when converted to the corresponding 1,2-epoxy-3-hydroxy-cyclohexane, may be dehydrogenated to form catechol. Substituted cyclohexenes yield the corresponding epoxyalcohols which can be dehydrogenated to yeild substituted dihydroxybenzenes.

This invention also relates to certain novel metal-exchanged catalyst per se which are useful in the aforedescribed epoxidation process.

Van Sickle et al, J. Catal. 19, 209 (1970), disclosed the use of cobalt-exchanged zeolites as catalysts for the unselective oxidation of olefins to form a mixture of ketones and unsaturated alcohols, along with a minor amount of epoxides in some cases. U.S. Pat. No. 3,641,066 (1972) teaches a similar process wherein molybdenum, tungsten, or vanadium-exchanged zeolite catalysts are employed in the formation of olefin epoxides. In neither case, however, are epoxy-alcohols obtained as reaction products. Finally, Belgian Pat. No. 640,204 and U.S. Pat. No. 3,259,638 teach the preparation of epoxyalcohols from olefins using as a catalyst system a compound derived from metals of Group IVA, VA, or VIA of the Periodic System, plus an alkylhydroperoxide and a radical initiator.

SUMMARY OF THE INVENTION

It has now been found, in accordance with the present invention, that acyclic and cyclic olefins may be oxidized to form the corresponding epoxyalcohols when there is employed as the catalyst a solid anionic material to which there is valence-bonded two different metals, one from Group IB or VIII, and the other from Group V of the Periodic Table.

The bi-metallic systems have the advantages that (1) they can be used without the need for added alkylhydroperoxides or initiators, (2) the solid catalyst is easily recoverable by filtration and may be reused many times without loss of activity, and (3) high yields of epoxyalcohols are possible using these catalyst systems.

DESCRIPTION OF THE INVENTION

The olefin starting material may be any linear or branched, cyclic or acyclic monoolefin or diolefin of the general formula

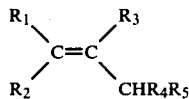

in which each of $R_1$, $R_2$, $R_3$, $R_4$, and $R_5$ may be the same or different, and are selected from the group consisting of hydrogen, lower alkyl, aryl, aralkyl, alkoxy, allyl, and alkenyl, and wherein $R_1$ and $R_3$ taken together may form a $C_5$ to $C_{10}$ cyclic hydrocarbon moiety. Included amongst these compounds are such olefins as tetramethylethylene, 2-ethylbutene-1, pentene-1, pentene-2, hexene-2, 2-methylpentene-2, 4-ethylpentene-2, cyclopentene, cyclohexene, methyl-substituted cyclohexenes, and fused ring alicyclic hydrocarbons such as dihydronaphthalene or indene. Preferred amongst these materials are cyclohexene and 1-methylcyclohexene.

When the aforedescribed olefins are oxidized in accordance with the process of the invention, there are obtained 1,2-epoxy-3-hydroxy derivatives of the general formula

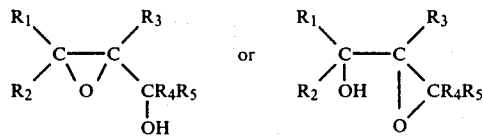

wherein each of $R_1$, $R_2$, $R_3$, $R_4$, and $R_5$ is as described above.

The catalyst used to effect the conversion of the aforesaid olefins to the epoxyalcohol is an ion-exchanged bimetallic solid catalyst, i.e., one in which the positive ions which are valence-bonded to an anionic support, as distinguished from conventional supported catalysts where the metal is deposited on, coated on, or precipitated with a neutral, non-ionic support such as pumice, carbon, kiesulguhr, alumina, or the like.

By "bimetallic" is meant that the anionic support must contain two different transition metal cations, each ionically bound to the support. One metal must be from Group V of the Periodic Table, and preferably is vanadium, while the other metal must be from Group IB or VIII, and preferably is cobalt, copper, iron, rhodium, ruthenium, osmium, or iridium.

The anionic support to which the metals are valence-bonded, may be any material having anionic sites which may be conveniently substituted with metals by conventional exchange methods. Thus, for example, suitable supports include faujasites, i.e., X- and Y-zeolites; mordenites, and ion-exchange resins, such as Amberlyst 15, and the like.

The catalyst of this invention may be prepared by any known exchange method wherein cations are substituted on anionic sites on the above-described supports. Thus, for example, using an X-type alumino-silicate zeolite as the support, a catalyst may be prepared by ion exchanging alkali metal-containing zeolites with transition metal ions which replace the alkali metal ions. Transition metal ion exchange can readily be effected, for example, with solutions of the salts of the metals such as their halides, sulfates, nitrates, and the like. Thus, for instance, a cobalt and vanadium exchanged X-zeolite catalyst may readily be prepared by first exchanging a sodium-exchanged X-zeolite with cobaltous chloride or nitrate until substantially all of the sodium is replaced by cobalt. The cobalt is then partially back-exchanged with a solution of a soluble vanadium salt such as vanadium oxysulfate to provide a zeolite containing both cobalt and vanadium ions in varying amounts depending on the quantity of vanadium used in the exchange.

The weight ratio of the two exchanged metals to each other on the anionic support is critical in the sense that for any given pair of metals there will be an optimum ratio which provides the fastest rate and an optimum ratio which provides for greatest selectivity of epoxyalcohols. These parameters can only be determined empirically by running a series of oxidations as desecribed herein, noting the rates and selectivities for each run, and then selecting the two values which provide the optimum results, preferably by first optimizing selectivity and then choosing the desired rate.

Thus, for example, a cobalt- and vanadium-exchanged X-zeolite catalyst was employed in the oxidation of cyclohexene to the corresponding epoxyalcohol, with the following results:

| Catalyst (0-15 Exchanges)* | % Co | % V | % Yield After 6 Hrs. | Selectivity to Epoxyalcohols |
|---|---|---|---|---|
| Co—V-0 | 15.5 | 0.0 | 30% | 0% |
| Co—V-1 | 14.8 | 1.1 | 36% | 39% |
| Co—V-5 | 9.4 | 3.9 | 33% | 50% |
| Co—V-10 | 4.6 | 5.6 | 16% | 52% |
| Co—V-15 | 4.0 | 6.5 | 6% | 53% |

*A cobalt zeolite exchanged with vanadium oxysulfate.

From this data it is apparent that for best yields and selectivity, ratios of Co-V of about 9 or 10 to 4 are desirable. Higher vanadium ratios give greater selectivity but slower rates.

The weight ratio of metal to support will vary depending upon the number of anionic sites available on the support which can be exchanged. This ratio should be maximized so that all possible anionic sites bear metal. In the case of X-zeolites, for instance, this represents about 15–20% by weight of metal based on the weight of the support.

These aforedescribed catalysts are essentially insoluble in the reaction medium employed in this process. They are, therefore, highly advantageous over the soluble prior art catalysts in that first, they are readily recoverable by filtration, and second, they are stable and may be reused many times without any loss of activity.

The oxidation of the olefins to form the corresponding epoxyalcohols is conveniently carried out in the liquid phase by bubbling air or oxygen into a solution containing the olefin and catalyst for a period of from 1 to 20 hours, depending upon the nature of the olefin starting material, at temperatures of from about 25° to 200° C., and preferably from 50° to 150° C. The oxygen is desirably bubbled through the solution at rates of 0.1 to 100 l./hr, and preferably 1–2 l./hr.

Oxygen pressure may also be used and the rate improved as a result. Pressures of up to 1000 psi cause accelerated rates and it is to be expected that higher pressures than this will cause further rate enhancement. Air can also be used in a similar manner but the rate is somewhat slower than with pure oxygen.

The resulting epoxyalcohol is conveniently recovered from the reaction mixture by, for example, vacuum distillation.

The amount of catalyst employed will generally range from about 1 to 10% by weight based on the weight of the olefin. However, it should be understood that this range is not a critical one and may be varied substantially depending upon the activity of the catalyst.

The novel process of this invention will now be illustrated by the following examples.

EXAMPLES

EXAMPLE 1—Formation of Epoxyalcohols from Olefins Using an X-Zeolite Exchanged with $Cu^{+2}$ and $V^{+4}$ (A) Preparation of the Catalyst 100 Grams of an X-zeolite whose acid sites are fully exchanged with sodium (15% Na by weight) is dried at 125° C. for 15 hours. A solution of 60.7 grams of $CuCl_2$ in 3300 cc of water is prepared. The sodium-X-zeolite is stirred in contact with 200 mls of the above solution at 40° C. for 30 min., filtered and the process repeated 15 times. After 16 copper exchanges the zeolite is washed until it is free of chloride ion and then it is dried at 125° C. for 15 hours. Analysis shows the sieve to be over 14% by weight of copper and less than 1% by weight of sodium. The dry copper-exchanged zeolite is labeled XZCu-OV.

The dry copper-exchanged X-zeolite is then exchanged in a similar manner at 40° C., 30 min. with a solution of 36.8 grams of vanadium oxysulfate in 1650 mls of water. The exchange process is summarized below, and recovered are four 25 gram batches of catalyst with varying ratios of copper to vanadium. This is accomplished by removing the proper amount of catalyst after 1, 5, 10 and 15 exchanges respectively.

| Exchange No. | Approx. cat. Wt. (gms) Used In Exchange | Total Solution |
|---|---|---|
| 1 | 100 | 300 |
| 2,3,4,5 | 75 | 600(4 × 150) |
| 6,7,8,9,10 | 50 | 500(5 × 100) |
| 11,12,13,14,15 | 25 | 250(5 × 50) |

After exchange 1, ¼ of catalyst is removed (catalyst : XZCu-1V)
After exchange 5, ⅓ of catalyst is removed (catalyst : XZCu-5V)
After exchange 10, ½ of catalyst is removed (catalyst : XZCu-10V)
After exchange 15, remaining catalyst is removed (catalyst : XZCu-15V)

All catalysts are then washed until sulfate-free then dried 15 hours at 125° C.

(B) Epoxyalcohol Formation Using an X-Zeolite Exchanged with $Cu^{+2}$ and $V^{+4}$ 1. Oxidation of Cyclohexene—Cyclohexene (12 ml) and the catalyst (each of those prepared above) (1 g) are charged to a glass reactor at 75° C. Oxygen is bubbled into the solution at a rate of 1.5 l./hr with vigorous stirring over a 5-hour period. The product mixture is analyzed by glpc. Products are separated by vacuum distillation and identified by combination of IR, NMRI, and mass spectral data as well as comparison of their g c retention times on columns of several substrates with those of known standards. The results of these reactions are summarized in Table I:

TABLE I

| Catalyst | Conversion, % | Selectivity to Epoxyalcohol, % |
|---|---|---|
| XZCu-0V | 41 | 0 |
| XZCu-1V | 21 | 30 |
| XZCu-5V | 20 | 48 |
| XZCu-10V | 12 | 39 |
| XZCu-15V | 7 | 33 |

Clearly the catalyst giving optimum rate and selectivity is XZCu-5V. The total product analysis for the optimum case is: conversion: 20%, selectivities: 1,2-epoxy-3-hydroxycyclohexane (48), cyclohexeneoxide (45), 1-cyclohexene-3-ol (3%) 1-cyclohexene-3-one (1%), polymer (4%).

2. Oxidation of Tetramethylethylene—Tetramethylethylene (12 ml) and the catalyst (XZCu-5V), (1 g) are charged to a 25 ml glass reactor at 50° C. Oxygen is bubbled into the solution at a rate of 1.5 l./min. with vigorous stirring over a 5-hour period. The olefin is converted (24%) to 1,2-epoxy-3-hydroxy-2,3-dimethylbutane in 46% yield. By-products are 2,3-epoxy-2,3-dimethylbutane (40%), 3-hydroxy-2,3-dimethylbutene (9%) and acetone (6%). Products were analyzed, identified, and separated as in 1-B-i above.

EXAMPLE 2—Formation of Epoxyalcohols from Olefins Using an X-Zeolite Exchanged with $Co^{+2}$ and $V^{+4}$ (A) Preparation of the Catalyst 100 grams of an X-zeolite which is 15% by weight cobalt and less than 1% by weight sodium is obtained from the sodium form by use of $CoCl_2$ in a procedure similar to that shown in Example 1(A). The dried cobalt-exchanged zeolite is labeled XZCo-OV.

The dried cobalt-exchanged-zeolite (50 g) is then exchanged 15 times with a solution of 18.4 grams vanadium oxysulfate in 825 mls. water as shown below:

| Exchange | Cat. Wt. | Total Solution |
|---|---|---|
| 1 | 50.0g | 150 ml |
| 2,3,4,5 | 37.5g | 300 ml (4 × 75) |
| 6,7,8,9,10 | 25.0g | 250 ml (5 × 50) |

| Exchange | Cat. Wt. | Total Solution |
|---|---|---|
| 11,12,13,14,15 | 12.5g | 125 ml (5 × 25) |

After 1 exchange removed ¼ cat. (12.5g of XZCo-1V)
After 5 exchanges removed ⅓ cat. (12.5g of XZCo-5V)
After 10 exchanges removed ½ cat. (12.5g of XZCo-10V)
After 15 exchanges removed remainder (12.5g of XZCo-15V)

| | Analyses of Catalyst | | |
|---|---|---|---|
| Catalyst | % Co | % V | % Na |
| XZCo-0V | 15.1 | 0.0 | 3.3 |
| XZCo-1V | 14.8 | 1.1 | 3.0 |
| XZCo-5V | 9.4 | 3.9 | 2.0 |
| XZCo-10V | 4.6 | 5.6 | 0.8 |
| XZCo-15V | 4.0 | 6.5 | 0.5 |

(B) Epoxyalcohol Formation Using an X-Zeolite Exchanged with $Co^{+2}$ and $V^{+4}$ (i) Oxidation of cyclohexene Oxidations are run under conditions identical to those of Example 1B(i)

| Catalyst | % Co | % V | % Yield After 6 Hrs. | Selectivity to Epoxyalcohol |
|---|---|---|---|---|
| Co—V-0 | 15.5 | 0.0 | 30 | 0% |
| Co—V-1 | 14.8 | 1.1 | 36 | 39% |
| Co—V-5 | 9.4 | 3.9 | 33 | 50% |
| Co—V-10 | 4.6 | 5.6 | 16 | 52% |
| Co—V-15 | 4.0 | 6.5 | 6 | 53% |

As noted earlier, it is evident that for best yields and selectivity, ratios of Co-V of about 9 or 10 to 4 are desirable. The total product analysis for the optimum case is: conversion: 33%, selectivities: cis-1,2-epoxy-3-hydroxycyclohexane (50%) cyclohexene oxide (39%), 1-cyclohexene-3-ol (2%) 1-cyclohexene-3-one (2%) polymer (;b 8%).

(ii) Oxidation of Tetramethylethylene

Tetramethylethylene (12 ml) and the catalyst, XZCo-5V (1 g) are charged to a 25 ml glass reactor at 50° C. Oxygen is bubbled into the solution at a rate of 1.5 l./min. with vigorous stirring over a 5-hour period. The olefin is converted (25%) to 1,2-epoxy-3-hydroxy-2,3-dimethylbutane in 45% yield. By-products are 2,3-epoxy-2,3-dimethylbutane (40%), 3-hydroxy-2,3-dimethylbutene (10%) and acetone (5%) (analysis by glpc).

(iii) Oxidation of Indene

Indene (12 mls) is oxidized by a gentle stream of oxygen (1.5 l./min.) over a 4-hour period at 75° C. using XZCo-5V (1 g) as the catalyst. It is converted (11%) to 1,2-epoxy-3-hydroxylhydrinene with a selectivity of 61%.

(iv) Oxidation of 3-Phenylpropene 3-phenylpropene (12 mls) in oxidized by a gentle stream of oxygen (1.5 l./min) over a 5-hour period at 100° C./using XZCo-5V (1 g) as the catalyst. It is converted (46%) to a mixture of 1,2-epoxy-3-hydroxy-3-phenylpropane and 2,3-epoxy-1-hydroxy-3-phenylpropane. The corresponding expoxides and allylic alcohols are minor by-products.

(v) Oxidation of 1-Methylcyclohexene and 1,2-Dimethylcyclohexene

According to procedures of Example 2-B(i), 1-methylcyclohexene and 1,2-dimethylcyclohexene were oxidized to epoxy-alcohols in 58 and 61% yield respectively and 41 and 45% conversion when the catalyst used was XZCo-5V.

EXAMPLE 3—Formation of Epoxyalcohols From Olefins Using an X-Zeolite Exchanged with $Fe^{+2}$ and $V^{+4}$ (A) Preparation of the Catalyst An X-Zeolite Exchanged with $Fe^{+2}$ and $V^{+4}$ 100 Grams of an X-zeolite whose acid sites are fully exchanged with sodium (15% Na by weight) is dried at 125° C. for 15 hours. A solution of 89.8 g $FeCl_2.4H_2O$ in 3300 ml distilled water is prepared. The sodium-X-zeolite is exchanged with 15 200 ml portions of this solution, washed until chloride free, then dried at 125° C. for 15 hours. Analysis shows the sieve to be over 14% by weight of iron and less than 10% by weight of sodium.

The dry iron-exchanged-X-zeolite is then exchanged 15 times at 40° C. for 30 minutes using a solution of 36.8 grams vanadium oxysulfate in 165 mls of water in a manner identical to example (1) above.

Similarly, four 25 gram samples of Fe-V containing catalyst are obtained.

(B) Oxidation of Cyclohexene

When cyclohexene is oxidized in a manner analogous to procedures used in Example 1-B(i), but substituting XZFe-5V as the catalyst, some 1,2-epoxy-3-hydroxycyclohexene is obtained together with other by-products. The catalyst, XZFe-5V, refers to an iron exchanged X-zeolite which has been subjected to give vanadium exchanges as shown in part A of this example.

EXAMPLE 4—Formation of Epoxyalcohols from Olefins Using a Y-Zeolite Exchanged with $Co^{+2}$ and $V^{+4}$ (A) Preparation of the Catalyst 50 grams of a Y-zeolite whose acid sites are fully exchanged with sodium (14% by weight of Na) is dried at 125° C. for 15 hours. The sodium ions are exchanged for cobalt ions by the method described above. Back-exchange of the cobalt with vanadium is accomplished in the manner of the previous examples to give 12.5 gram samples having varying amounts of cobalt and vanadium bound to the Y-zeolite.

| Catalyst | % Co | % V |
|---|---|---|
| YZCo-0V | 14.8 | 0.0 |
| YZCo-1V | 12.6 | 1.0 |
| YZCo-5V | 8.3 | 3.6 |
| YZCo-10V | 4.8 | 5.8 |
| YZCo-15V | 3.9 | 7.3 |

(B) Oxidation of Cyclohexene

Using YZCo-5V according to the procedure of Example 1B(i), cyclohexene is oxidized to 1,2-epoxy-3-hydroxy-cyclohexene in high yield.

EXAMPLE 5—Formation of Epoxyalcohols from Olefins Using a Mordenite Exchanged with $Co^{+2}$ and $V^{+4}$ (A) Preparation of the catalyst 50 grams of ZEOLIN-Na, a sodium exchanged synthetic mordenite having the general formula, Na$_2$O.Al$_2$O$_3$.10SiO$_2$, is exchanged with COCL$_2$ in a manner identical to that described in Example (3) to form a cobalt-exchanged mordenite having most of the sodium ions replaced by cobalt. The catalyst at this point is mainly: CoO.Al$_2$O$_3$.10SiO$_2$ after drying.

The dry cobalt-exchanged mordenite is then exchanged 15 times at 40° C. for 30 minutes with a solution of 18.5 grams vanadium oxysulfate in 5 mls of water in a manner identical to examples (1), (2), and (3) above.

Similarly, four 12.5 gram samples of Co-V exchanged mordenite catalysts are obtained.

(B) Oxidation of Cyclohexene

Using MCo-5V according to the procedure of Example 1V(i), cyclohexene is oxidized to 1,2-epoxy-3-hydroxy-cyclohexene in 66% yield.

EXAMPLE 6—Formation of Epoxyalcohols from Olefins Using an Amberlyst Resin Exchanged with Rh$^{+3}$ and V$^{+4}$ (A) Preparation of the Catalyst Amberlyst-15 beads (a divinylbenzene cross-linked polystyrene matrix having co-polymerized divinylbenzene therein to which are attached nuclear sulfonic acid groups, Rohm and Haas) (50 g.) are gently swirled in an excess of an alkaline solution of sodium hydroxide for 24 hours. Gentle swirling is necessary to avoid mechanical grinding and destruction of the beads. Over 90% of the sulfonic acid groups are replaced with sodium ions in this manner.

Sodium-exchanged Amberlyst beads are gently swirled at 50° C. in the presence of methanol solutions of rhodium trichloride until most of the sodium was replaced. The rhodium-exchanged resin is partially exchanged with methanol solutions of vanadium oxysulfate resulting in catalyst for varying Rh/V ratios.

(B) Oxidation of Tetramethylethylene

Using ARh-5V according to the procedures of Example 1B(ii), tetramethylethylene is oxidized to 2,3-epoxy-3-hydroxy-2,3-dimethylbutane in good yield.

The invention claimed is:

1. In a process for the oxidation of acyclic and cyclic monoolefins and corresponding diolefins to form the corresponding epoxyalcohols by the catalytic oxidation of olefins with air or oxygen, the improvement wherein the catalyst comprises a solid anionic support material having valence-bonded thereto two different transition metal cations, one of which is from Group IB or Group VIII of the Periodic Table, the other of which is from Group VB of the Periodic Table, wherein the monoolefin is of the general formula

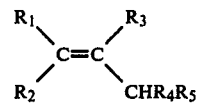

wherein each of R$_1$, R$_2$, R$_3$, R$_4$ and R$_5$ may be the same or different and are selected from the group consisting of hydrogen, lower alkyl, aryl, aralkyl, alkoxyl, and alkenyl, and wherein R$_1$ and R$_3$ are taken together may be a C$_5$ to C$_{10}$ cyclic hydrocarbon moiety, and the resulting epoxyalcohol is of the formula

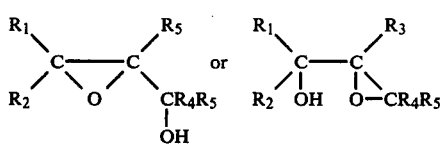

wherein R$_1$, R$_2$, R$_3$, R$_4$ and R$_5$ are as defined above.

2. The process according to claim 1 wherein the olefin starting material is selected from the group consisting of tetramethylethylene, 2-ethylbutene-1, pentene-1, pentene-2, hexene-2, 2-methylpentene-2, 4-ethylpentene-2, cyclopentene, cyclohexene, methyl-substituted cyclohexene, dihydronaphthalene, and indene.

3. The process according to claim 1 wherein one of the metals is vanadium and the other is selected from the group consisting of cobalt, copper, iron, rhodium, ruthenium, osmium, and iridium.

4. The process according to claim 1 wherein the anionic support material of the catalyst is a faujasite, a mordenite, or an ion-exchange resin.

5. The process according to claim 4 wherein the faujasite is an X-zeolite or a Y-zeolite.

6. The process according to claim 1 wherein the catalyst is a cobalt- and vanadium-exchanged X-zeolite.

7. The process according to claim 1 wherein the catalyst is a copper- and vanadium-exchanged X-zeolite.

8. The process according to claim 1 wherein the catalyst is a cobalt- and vanadium-exchanged Y-zeolite.

9. The process according to claim 1 wherein the catalyst is an iron- and vanadium-exchanged X-zeolite.

10. The process according to claim 1 wherein the catalyst is a cobalt- and vanadium-exchanged mordenite.

11. The process according to claim 1 wherein the catalyst is a rhodium- and vanadium-exchanged ion-exchange resin.

12. The process according to claim 1 wherein the catalyst employed is in the amounts of from about 1 to 10% by weight based on the weight of the olefin.

13. The process according to claim 1 wherein the oxidation is carried out under oxygen or air pressure.

14. The process according to claim 1 wherein the catalyst is a cobalt- and vanadium-exchanged X-zeolite containing about 9.0% cobalt by weight, about 4.0% vanadium by weight, and about 2.0% sodium by weight, and wherein the monoolefin is cyclohexene to provide cis-1,2-epoxy-3-hydroxycyclohexane.

* * * * *